United States Patent [19]

Nazareth et al.

[11] Patent Number: 5,739,041
[45] Date of Patent: Apr. 14, 1998

[54] DIAGNOSTIC DETECTION DEVICE

[75] Inventors: Albert Nazareth, Mercerville, N.J.; Yea-Shun Cheng, Doylestown, Pa.; Mary Beth Boyle, Pennington, N.J.

[73] Assignee: Carter Wallace, Inc., New York, N.Y.

[21] Appl. No.: 432,890

[22] Filed: May 2, 1995

[51] Int. Cl.$^6$ .................................................. G01N 33/53
[52] U.S. Cl. ..................... 436/518; 422/58; 435/7.1; 435/7.5; 435/7.92; 435/7.94; 435/970; 436/510; 436/518; 436/530; 436/525; 436/541; 436/807; 436/810
[58] Field of Search ................... 422/55–58, 68.1, 422/69–70; 435/7.1, 7.5, 7.92, 7.94–7.95, 805, 970, 971; 436/510, 528–32, 541, 164–65, 169, 518, 525

[56] References Cited

U.S. PATENT DOCUMENTS

| | | | |
|---|---|---|---|
| D. 341,663 | 11/1993 | Coulter | D24/225 |
| 3,655,515 | 4/1972 | Noorlander | 195/103.5 |
| 3,811,840 | 5/1974 | Bauer et al. | 23/253 |
| 4,301,812 | 11/1981 | Layton et al. | 128/761 |
| 4,366,241 | 12/1982 | Tom et al. | 435/7.9 |
| 4,446,232 | 5/1984 | Liotta | 435/7.9 |
| 4,594,327 | 6/1986 | Zuk | 436/514 |
| 4,624,929 | 11/1986 | Ullman | 436/179 |
| 4,703,017 | 10/1987 | Campbell et al. | 436/501 |
| 4,756,828 | 7/1988 | Litman et al. | 435/7.9 |
| 4,757,004 | 7/1988 | Houts et al. | 435/7.9 |
| 4,857,453 | 8/1989 | Ullman et al. | 435/7.9 |
| 4,861,711 | 8/1989 | Friesen et al. | 435/970 |
| 4,956,302 | 9/1990 | Gordon et al. | 436/161 |
| 4,960,691 | 10/1990 | Gordon et al. | 435/6 |
| 4,981,786 | 1/1991 | Dafforn et al. | 435/7.9 |
| 4,999,285 | 3/1991 | Stiso | 435/7.9 |
| 5,075,078 | 12/1991 | Osikowicz et al. | 422/56 |
| 5,079,142 | 1/1992 | Coleman et al. | 435/7.92 |
| 5,104,813 | 4/1992 | Besemer et al. | 436/179 |
| 5,120,504 | 6/1992 | Petro-Roy et al. | 422/58 |
| 5,120,643 | 6/1992 | Ching et al. | 435/7.92 |
| 5,141,850 | 8/1992 | Cole et al. | 436/525 |
| 5,164,294 | 11/1992 | Skold et al. | 435/7.5 |
| 5,232,835 | 8/1993 | Litman et al. | 435/7.93 |
| 5,248,619 | 9/1993 | Skold et al. | 436/514 |
| 5,354,692 | 10/1994 | Yang et al. | 436/514 |
| 5,356,782 | 10/1994 | Moorman et al. | 435/7.9 |
| 5,384,264 | 1/1995 | Chen et al. | 436/525 |
| 5,459,080 | 10/1995 | Adamczyk et al. | 436/538 |
| 5,602,040 | 2/1997 | May et al. | 436/514 |

FOREIGN PATENT DOCUMENTS

| | | |
|---|---|---|
| 0 271 204 A2 | 6/1988 | European Pat. Off. |
| 0 291 194 A1 | 11/1988 | European Pat. Off. |
| 0 299 428 A2 | 1/1989 | European Pat. Off. |
| 0 420 021 A2 | 4/1991 | European Pat. Off. |
| 0 505 636 A1 | 9/1992 | European Pat. Off. |
| 2 204 398 B | 11/1988 | United Kingdom. |
| WO 88/08534 | 11/1988 | WIPO. |
| WO92/01226 | 1/1992 | WIPO ..................... G01N 33/558 |

OTHER PUBLICATIONS

International Search Report for corresponding PCT application serial No. PCT/US96/06086.

Lou et al. (1993) "One-Step Competitive Immunochromatographic Assay for Semiquantitative Determination of Lipoprotein(a) in Plasma," *Clinical Chemistry* 39: 619–624.

*Primary Examiner*—Carol A. Spiegel
*Attorney, Agent, or Firm*—Testa, Hurwitz & Thibeault, LLP

[57] ABSTRACT

The invention is an improved single-step test device for detecting the presence of a pre-selected analyte in a urine stream. The device has a hollow outer casing and an assay material disposed within the casing. The outer casing defines: a urine inlet port; a viewing window; and at least one drainage vent spaced about the urine inlet port. The assay material is a sorptive material defining: a urine sample application region adjacent to, and in fluid communication with the urine inlet port; a capture region adjacent to the viewing window; and a fluid flow path for transporting liquid sample between the urine sample application region and the analyte capture region. The drainage vent is located to permit excess urine entering the casing from the urine stream to exit the casing thereby to minimize hydraulic pressure induced flooding of the assay material disposed within the casing and to reduce the frequency of false test results.

16 Claims, 3 Drawing Sheets

DIAGNOSTIC DETECTION DEVICE

FIELD OF THE INVENTION

This invention relates to an improved device for assaying a pre-selected analyte, such as an antigen, in a body fluid, such as urine. More particularly, the present invention relates to a device having a novel flow through cell that prevents hydraulic pressure induced flooding of assay material disposed within the device when urine is applied from a urine stream directly onto the assay material.

BACKGROUND OF THE INVENTION

A variety of ligand-receptor assays have been developed to detect the presence of a pre-selected analyte in body fluid. Typically, these assays involve antibody-antigen interactions, synthetic conjugates comprising radioactively, enzymatically, spectroscopically, or visually observable tags, and specially designed reactor chambers. In most assays, there is a receptor (e.g., an antibody) that is specific for the pre-selected analyte (e.g., an antigen), and a means for detecting the presence and/or amount of a resulting receptor-analyte (e.g., antibody-antigen) complex. Most current assays are designed to make a quantitative determination, but in many circumstances all that is required is a qualitative result, i.e., a positive or negative signal. Examples of such qualitative assays include, for example, pregnancy tests, ovulation tests as well as a variety of other types of urine analysis. In these tests, visually observable signals such as the presence of agglutination or a color change are preferred.

The assays optimally are performed using single-step devices wherein the only step the user need perform prior to observation of the result is application of the sample to be assayed onto the device. Single-step devices, therefore, obviate the necessity of performing, subsequent to the application of the sample, a series of manipulations which may be time consuming and/or may introduce errors in the end result. Accordingly, several single-step devices, for example those described in Int'l Appl. Publ. Nos.: WO 088/08534, published Nov. 3, 1988, have been developed and are commercially available.

The single-step device described in Int'l Appl. Publ. No. WO88/08534 comprises a hollow casing containing a porous assay material communicating with the exterior of the casing via a fluid sample receiving member. During operation, the user applies the fluid test sample onto the fluid sample receiving member protruding out of the casing. Thereafter, the fluid sample while traversing the carrier material enters the casing and moves to a capture region disposed upon the carrier material. The capture region comprises a means for binding a pre-selected analyte. When the fluid sample reaches the capture region, assuming that the fluid sample contains the analyte, the analyte binds to the capture region. The bound analyte subsequently can be visualized within the capture region.

It has been found, however, that invalid test results may arise from the use of single-step devices, particularly devices wherein the fluid sample is applied directly from a fluid stream through a urine inlet port defined by the casing onto assay material enclosed therein. Accordingly, it is an object of the present invention to provide an improved single-step detection device for reliably detecting the presence of a pre-selected analyte within a body fluid, when the body fluid i.e., urine, is applied directly from a fluid stream, i.e., a urine stream, onto assay material disposed within device. It is another object of the invention to provide a method for detecting a pre-selected analyte using a single-step device of the type described herein. It is another object of the invention to provide a method for producing a single-step detection device of the type described herein.

These and other objects and features of the invention will be more clearly understood from the description, drawings, and claims which follow.

SUMMARY OF THE INVENTION

The present invention provides a rapid, sensitive and more reliable device and method for detecting the presence of analytes in a fluid stream. The use of the present device and method provide a system for measuring the presence of a pre-selected analyte in body fluid, specifically urine, which involves a minimal number of procedural steps, and reproducibly yields reliable results even when used by untrained persons.

It has been discovered that during the use of single-step devices, particularly devices wherein the sample of fluid to be assayed is applied directly from a stream of fluid onto assay material enclosed within the device casing, false or otherwise invalid results may arise following hydraulic pressure induced flooding of assay material. The incidence of flooding impairs the reliability, and therefore the commercial value of the test kit. Accordingly, the single-step device and method of the instant invention utilize an improved device casing that minimizes hydraulic pressure induced flooding of the assay material located therein thereby to increase significantly the reliability of the test result. More specifically, it has been discovered that introduction of drainage vents in the casing dramatically improves the reliability of the test kit and virtually eliminates the incidence of flooding.

In its broadest aspect, the invention provides a device having an outer casing and an assay material disposed within the casing for detecting the presence of an analyte in a urine stream. The assay material defines a capture region for binding the analyte. The outer casing defines the following features which include: (1) a hollow housing enclosing the assay material; (2) a urine inlet port to permit urine applied directly from a urine stream to enter the casing and contact the assay material disposed within the casing; (3) a window spaced apart from the urine inlet port for viewing the capture region and (4) at least one drainage vent to permit excess urine entering the casing through the urine inlet port to exit the casing thereby to minimize hydraulic pressure induced flooding of the casing.

In a preferred embodiment, the assay material comprises a sorptive material defining a urine sample application region spaced apart from the capture region. The sorptive material permits the sorptive transport of urine between the urine sample application region and the capture region. Therefore, when urine from a urine stream is directed through the urine inlet port onto the urine sample application region the analyte in the urine moves by sorptive transport from the urine application region to the capture region, whereupon the analyte binds to the capture region.

In another embodiment, the device casing defines three drainage vents spaced about the urine inlet port to permit urine entering the casing via the urine inlet port to exit the casing. The drainage vents, therefore, minimize the build up of urine within the casing and thereby inhibit hydraulic pressure induced flooding of the assay material disposed therein. In another embodiment, the window for viewing the capture region is located on a side of the device casing opposite the urine inlet port.

In another embodiment, the device further comprises a rib member defining a dam positioned within the casing to inhibit hydraulically driven urine from flooding the casing. The rib member may either be defined by an inner surface of the casing formed during the production of the casing or may be a separate component inserted into the device during assembly.

In a preferred aspect, the invention provides a device having an outer casing and an assay material disposed within the casing for detecting the presence of an analyte in a urine stream. The outer casing defining the following features which include: (1) a hollow housing for receiving the assay material; (2) a urine inlet port at a proximal end of the casing to permit urine applied directly from a urine stream to enter the casing; (3) a window at a distal end of the casing for viewing a capture region on the assay material; and (4) at least one drainage vent to permit excess urine entering the casing through the urine inlet port to exit the casing thereby to minimize hydraulic pressure induced flooding of the casing. The assay material enclosed within the casing defines (1) a urine sample application region, (2) an analyte capture region and (3) a fluid flow path connecting the urine sample application region and the analyte capture region. The urine sample application region is located adjacent to, and in fluid communication with the urine inlet port whereas the analyte capture region is located adjacent to the viewing window. The fluid flow path transports the urine sample by sorption between the urine sample application region and the capture region such that when a urine stream is directed through the inlet port onto the urine sample application region, the analyte in the urine moves by sorptive transport along the flow path of the assay material to the capture region whereupon the analyte binds to the capture region.

In another aspect, the invention provides a method for detecting the presence of an analyte in a urine stream suspected to contain the analyte. The improvement comprises employing an improved device of the type described herein.

In another aspect, the invention provides a method for producing an improved device for detecting the presence of an analyte in a urine stream. The method comprises the steps of providing an assay material having a capture region for binding the analyte and providing a casing. The casing defines (1) a hollow housing for receiving the assay material, (2) a urine inlet port to permit urine applied directly from a urine stream to enter the casing, (3) a window spaced apart from the urine inlet port for viewing the capture region, and (4) at least one drainage vent to permit urine entering the casing through the urine inlet port to exit the casing thereby to minimize hydraulically induced flooding of the casing. The method further comprises the step of enclosing the assay material within the casing.

BRIEF DESCRIPTION OF THE DRAWINGS

The present invention will now be more particularly described with reference to and as illustrated in, but in no manner limited to, the accompanying drawings, in which.

In the drawings, like reference characters in the respective drawings indicate corresponding parts.

DETAILED DESCRIPTION OF THE INVENTION

In its most general application, the present invention provides an improved single-step device for detecting a pre-selected analyte in a urine stream. More specifically, use of the invention provides an easily readable, sensitive, and reproducible indication of the presence of an analyte, such as, human chorionic gonadotropin (hCG) or luteinizing hormone (LH), in a urine stream.

As described hereinabove, the use of a single-step device, specifically a single-step device wherein the urine sample to be assayed is applied directly from a urine stream through a urine sample inlet port onto assay material enclosed within the casing of the device, may result in false or otherwise invalid test results. Recently, it has been discovered that the invalid test results may occur when the operator applies too much sample to the device which in turn results in flooding of the assay material enclosed within the device casing. Without wishing to be bound by theory, it is believed that the flooding of the assay material prevents the sequential series of reactions that occur between the analyte and the analyte visualization reagents and/or the analyte capture reagents under optimal assay conditions. Accordingly, the single-step device and methods of the instant invention utilize an improved device casing that minimizes hydraulic pressure induced flooding of the assay material located within the casing thereby increasing the reliability of the test result.

In its broadest aspect, the improved device comprises an outer casing and an assay material disposed therein. The assay material defines a capture region for binding an analyte of interest, i.e., hCG or LH. The outer casing defines the following elements which include: a hollow housing for receiving the assay material; a urine inlet port to permit urine applied directly from a urine stream to enter the casing and to contact the assay material; a window for viewing the capture region on the assay material; and at least one drainage vent to permit urine entering the casing via the urine inlet port exit the casing thereby to inhibit hydraulic pressure induced flooding of the casing.

As used herein, the term "urine inlet port" is understood to mean any aperture defined by the outer casing that connects the hollow interior of the casing with the exterior of the casing. The urine inlet port, therefore, permits urine applied directly from a stream of urine to enter the casing and to contact assay material disposed therein. As used herein, the term "window" is understood to mean any aperture defined by the outer casing that connects the hollow interior of the casing with the exterior of the casing for viewing a capture region of the assay material, when the assay material is disposed within the casing. In a preferred embodiment the window for viewing the capture region of the assay material is spaced apart from the urine inlet port, however, it is anticipated that in certain configurations the window and the urine inlet port may be defined by a single aperture. In the preferred embodiment, the urine inlet port and the viewing window are spaced apart such that urine inlet port and the viewing window are located on opposite sides of the casing. This configuration reduces the incidence of contamination of the capture region which is disposed in the interior of the casing.

The casings useful in the practice of the instant invention, in addition, comprise means for minimizing hydraulically induced flooding of the test system when a urine stream is directed through the urine inlet port onto assay material disposed within the casing. The invention therefore embraces any means that prevents flooding of the assay material disposed therein.

In the preferred embodiment, the means for minimizing the hydraulically induced flooding of the casing comprises at least one drainage vent. As used herein, the term "drainage vent" is understood to mean any aperture defined by the outer casing that connects the hollow interior of the casing with the exterior of the casing and permits excess urine entering the casing through the urine inlet port to exit the casing. The drainage vent, therefore, dissipates the hydraulic pressure of the urine entering the casing and minimizes hydraulic pressure induced flooding of the assay material disposed therein. As used herein, the term "hydraulic pressure induced flooding" is understood to mean the accumulation of urine within the hollow casing when urine from a urine stream is directed into the casing in an amount sufficient to flood the assay material disposed therein.

The casing, therefore, may comprise one or more drainage vents which, either alone or in combination, permit urine entering the casing through the urine inlet port to exit the casing thereby to dissipate the hydraulic pressure of the urine. Although it is anticipated that a variety of drainage vent configurations may be effective in dissipating the hydraulic pressure of urine entering the casing, the drainage vents preferably are spaced about the urine inlet port. In addition, the drainage vents preferably are located upstream of a capture region disposed upon the assay material, and most preferably are located upstream of a release region also disposed upon the assay material. As described hereinbelow, the release region on the assay material is located upstream of the capture region, therefore, if a drainage vent is upstream of the release region the drainage vent inherently is located upstream of the capture region. In the currently preferred embodiment of the invention, the casing defines a plurality of drainage vents, specifically three drainage vents, spaced about the urine inlet port to permit urine entering the casing via the fluid inlet port to exit the casing and to minimize hydraulic pressure induced flooding of the assay material disposed within the casing.

In another embodiment, the means for minimizing hydraulically induced flooding of the casing comprises a rib member that acts either on its own or in combination with a drainage vent. As used herein, the term "rib member" is understood to mean any structural element in the casing, for example, a dam, that blocks or prevents hydraulically driven urine from flooding the assay material. Accordingly, the rib member provides another means for minimizing the amount of urine that traverses the assay material by a mechanism other than by sorptive transport.

The rib member may be defined either by one or more inner surfaces of the casing or may comprise a separate element that is inserted into the casing during assembly of the device. It is contemplated that whenever the rib is defined by an inner surface of the casing, the rib member is produced during the formation of the outer casing. In such a case, it is contemplated, therefore, that the rib is defined by the same moisture impervious material as is the outer casing. However, when the rib member is a separate element inserted into the casing during assembly of the device, it is anticipated that the rib may be produced from a moisture impermeable material other than the material used to produce the casing.

From the foregoing, it is appreciated that the outer casing of the device may take various forms. Typically, it will comprise an elongate casing comprising interfitting parts made of a moisture impervious solid materials, for example, a plastic material. It is contemplated that a variety of commercially available plastics, including, but not limited to, polyvinyl chloride, polypropylene, polystyrene, polyethylene, polycarbonates, polysulfanes, polyesters, urethanes, and epoxies maybe used to produce casings useful in the practice of the instant invention. The device casings may be prepared by conventional methodologies, for example, standard molding technologies well known and used in the art. For example, the casings may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, *Processes And Materials of Manufacture*, Third Edition, R. A. Lindsberg (1983) Allyn and Baron pp. 393–431.

The device of the present invention will now be described in greater detail with reference to the attached drawings, which are provided for purposes of illustration and not meant to be limitation on the scope of the present invention.

Referring to the drawings, FIGS. 1A–1F illustrate schematically a first embodiment of a test device 5 constructed in accordance with the teachings of the present invention. The device comprises two interfitting sections 10 and 20 wherein 10 is an upper section of the casing and 20 is a lower section of the casing. Conveniently, the two sections may include means for interlocking the two sections together. For example, the inner surface of one of the sections may contain protrusions which are designed to snap fit into protrusion receiving means located on the inner surface of the other section. The two sections 10 and 20, when interconnected, produce an outer casing that defines a hollow enclosure for receiving an assay material.

Figure 1A:
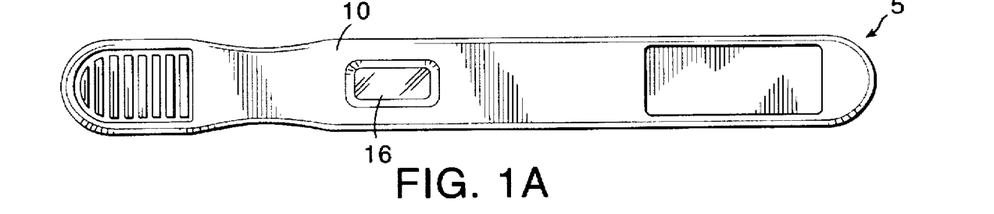
FIG. 1A is a top view of a first embodiment of a casing useful in the device of the present invention showing the viewing window.
Figure 1B:
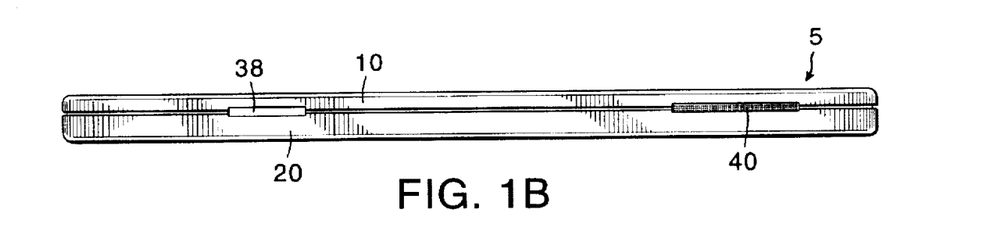
FIG. 1B is a longitudinal side view of the device of FIG. 1A showing the drainage vent.
Figure 1C:
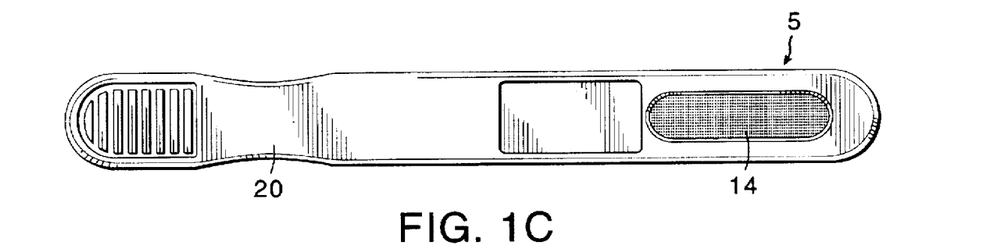
FIG. 1C is a bottom view of the device of FIG. 1A showing the urine inlet port.
Figures 1D, 1E, 1F:
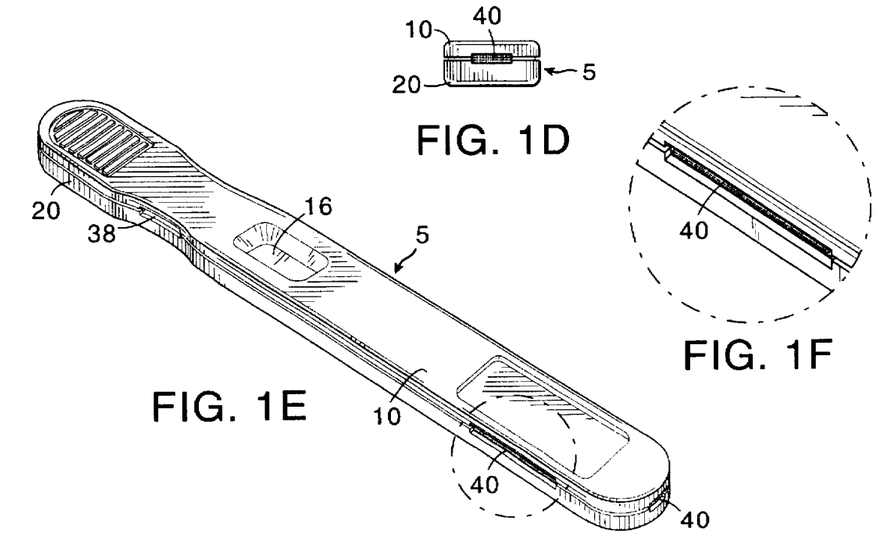
FIG. 1D is an end view of the proximal end of the device of FIG. 1A showing a drainage vent.
FIG. 1E is a perspective view of a currently preferred device constructed in accordance with the present invention.
FIG. 1F is an exploded perspective view showing the drainage vent.
Figure 2A:
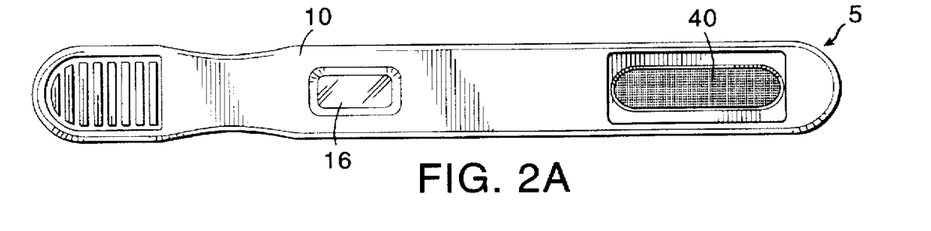
FIG. 2A is a top view of a second embodiment of a casing useful in the device of the present invention showing a drainage vent and a viewing window.
Figure 2B:
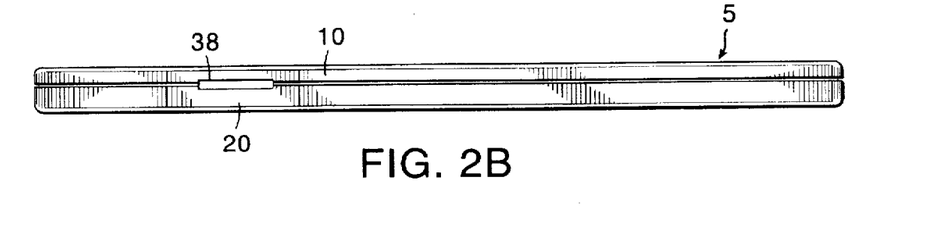
FIG. 2B is a longitudinal side view of the device of FIG. 2A.
Figure 2C:
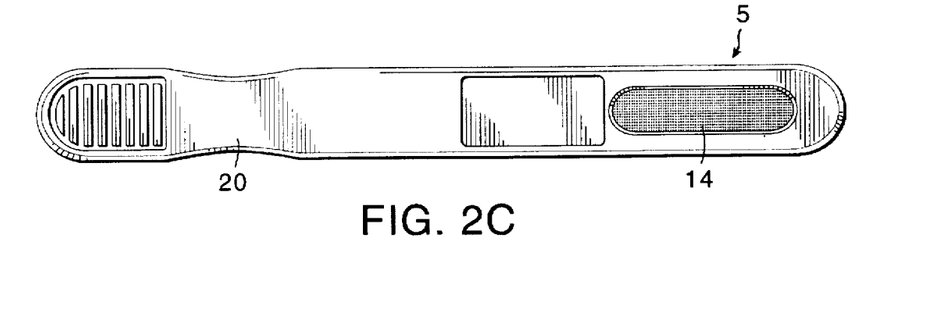
FIG. 2C is a bottom view of the device of FIG. 2A showing the urine inlet port.
Figures 2D, 2E:
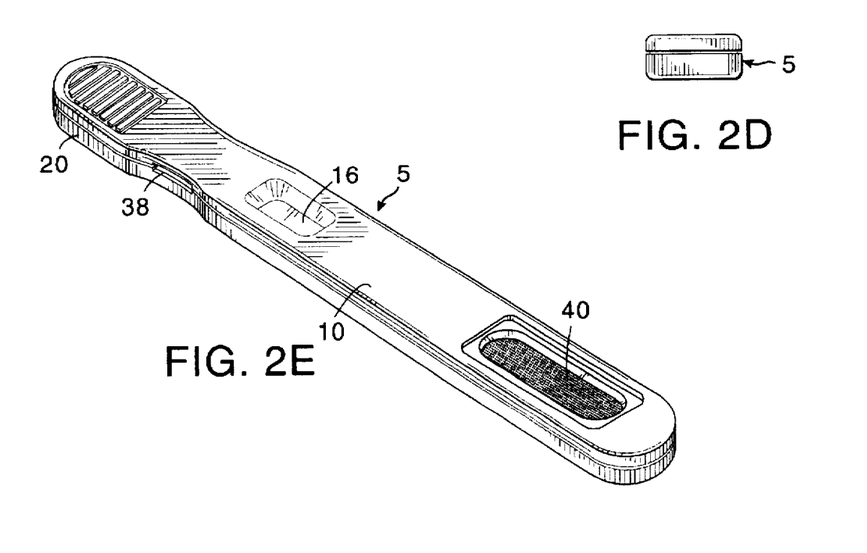
FIG. 2D is an end view of the proximal end of the device of FIG. 2A.
FIG. 2E is a perspective view of a device constructed in accordance with the present invention.
Figure 3A:
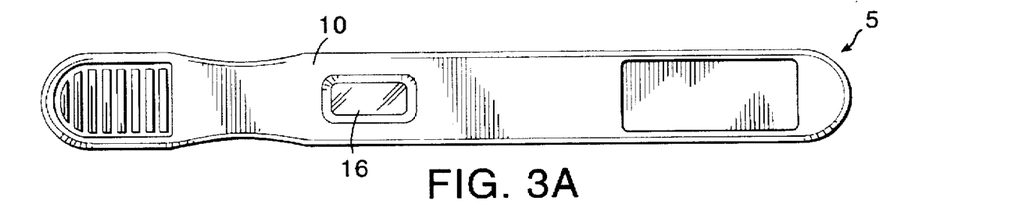
FIG. 3A is a top view of a third embodiment of a casing useful in the device of the present invention showing the window opening.
Figure 3B:
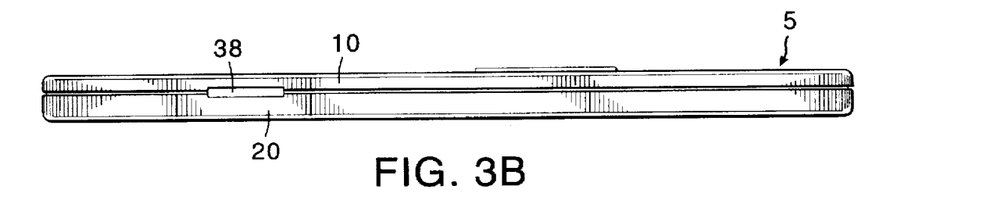
FIG. 3B is a longitudinal side view of the device of FIG. 3A.
Figure 3C:
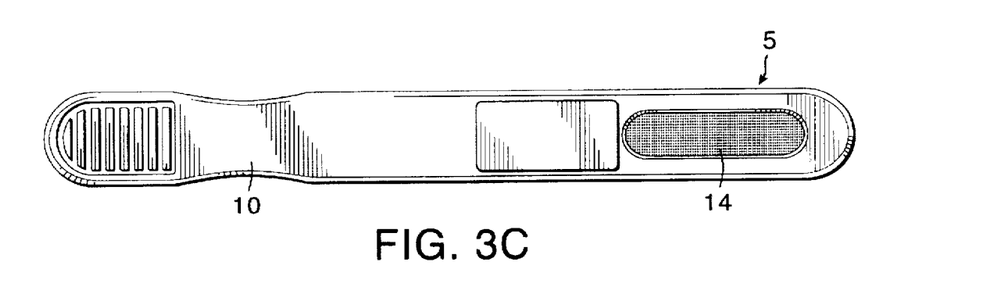
FIG. 3C is a bottom view of the device of FIG. 3A showing the urine inlet port.
Figures 3D, 3E:
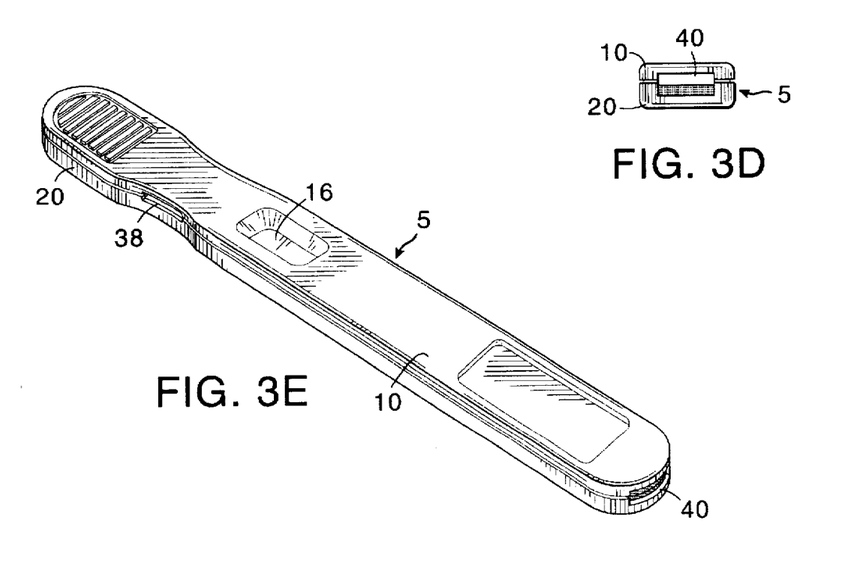
FIG. 3D is an end view of the proximal end of the device of FIG. 3A showing the drainage vent.
FIG. 3E is a perspective view of a device constructed in accordance with the present invention.

In addition, the outer casing defines a fluid inlet port 14 at a proximal end of the casing and a window 16 at a distal end of the casing through which the capture region on the assay material is visible. As illustrated in FIGS. 1A, 1C, and 1E, window 16, defined by the upper section of the casing 10, and fluid inlet port 14, defined by the lower section of the casing 20, are disposed on a opposite sides of the casing. This configuration reduces the incidence of contamination of the capture region which is disposed in the interior of the casing. The casing further defines two air displacement openings 38, each of which are located at a distal end of the casing on the sides of the casing where the upper section of the casing 10 mates with the lower section of the casing 20. The air displacement openings 38 permit air displaced by the addition of urine to the assay material to exit the casing. The casing further defines three drainage vents 40, spaced about the fluid inlet port 14. In this embodiment, one drainage vent is located at the extreme proximal end of the device 5 with the other two drainage vents located in the sides of the device, specifically, where the upper section of the casing 10 mates with the lower section of the casing 20. One of the latter drainage vents 40 is shown in the exploded perspective view, FIG. 1F. The drainage vents are located to permit urine entering the casing through the urine inlet port 14 to exit the casing thereby inhibiting hydraulic pressure induced flooding of the casing. The presence of the drainage vents 40, therefore, reduce flooding of the assay material disposed in the casing when the user applies too much sample to the device.

Referring to the drawings, FIGS. 2A-2E and 3A-3E illustrate schematically a second and a third embodiment of the invention, respectively. The first, second and third embodiments differ only in the number and location of the drainage vents 40 defined by the casing. For example, in embodiment 2, FIGS. 2A-2E show a single drainage vent 40 disposed apart from the window 16 in the upper section of the casing 10. In the second embodiment, the drainage vent 40 in the upper section of the casing 10 is positioned directly above the urine inlet port 14 in the lower section of the casing 20. In the third embodiment, FIGS. 3A-3E show a single drainage vent 40 located at the extreme proximal end of the device 5 where the upper section of the casing 10 mates with the lower section of the casing 20.

It is contemplated that the casing may further define a control opening located downstream of, or distal to the window opening for viewing a control region disposed on the assay material. Accordingly, the control region preferably is disposed upon the assay material downstream of the analyte capture region. The control regions enable the user to determine whether the device has functioned properly during usage. Preferred control regions and the preferred reagents used therein are described in U.S. patent application, U.S. Ser. No. 08/432,894, filed on even date herewith, the disclosure of which is incorporated herein by reference.

As used herein, the term "assay material" is understood to mean any material, preferably a sorptive material, that can be used to detect the presence of a pre-selected analyte in a urine sample. As used herein, the term "capture region" is understood to mean a region of the assay material capable of binding, either directly or indirectly, the pre-selected analyte. During direct binding, the pre-selected analyte binds to an immobilized binding partner, for example, an anti-analyte antibody immobilized within the capture region of the assay material. During indirect binding, the pre-selected analyte binds to a binding partner, for example, an anti-analyte antibody-biotin conjugate, and the binding partner binds to a capture component, for example, streptavidin, immobilized within the capture region of the assay material.

As described herein, the assay material may further define a urine sample application region. As used herein, the term "urine sample application region" is understood to mean a region, that preferably is disposed apart from the capture region and positioned within the casing such when urine is applied directly from a urine stream to the urine inlet port, the urine enters the casing and contacts the urine sample application region. The urine application region and the capture region preferably are connected by a fluid flow path. The fluid flow path permits urine that contacts the urine sample application region to flow to the capture region by means of sorptive transport. Accordingly, it is understood that the capture region of the assay material is located downstream of the urine sample application region.

It is contemplated that the assay material may comprise either a single element which when enclosed within the casing is capable of detecting the presence of analyte in a urine sample. Alternatively, the assay material may comprise several elements which when enclosed within the casing cooperate with one another during the detection of the analyte in urine sample. For the purpose of understanding the present invention, however, the selection of the assay material is not critical, and indeed, it is contemplated that the invention may utilize a variety of assay materials well known and described in the art.

In a particularly preferred embodiment, the assay material comprises three cooperating elements, specifically a urine sample absorbent material, a biphasic chromatographic substrate, and a reservoir absorbent material, all of which are described in detail in copending application U.S. Ser. No. 08/432,894. The urine sample absorbent material, the biphasic chromatographic substrate and the reservoir absorbent material are all in fluid communication with one another so that urine applied to the urine sample absorbent material traverses the biphasic chromatographic substrate by sorptive transport until it reaches the reservoir absorbent material.

In the preferred embodiment, the urine sample absorbent material is disposed within the casing adjacent to, and in fluid communication with the urine sample inlet port and, therefore, acts as the urine sample application region. The absorbent material of the urine sample application region may further act as a filter to remove impurities, particulate matter and interference factors from the urine sample. The urine sample absorbent material preferably is a bibulous hydrophilic material which facilitates absorption and transport of the urine sample to the biphasic chromatographic medium. Such materials may include cellulose acetate, hydrophilic polyester, or other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Ahlstrom 939 or Ahlstrom 1281. The sample absorbent preferably is coated with a buffered solution containing bovine serum albumin (BSA) and a nonionic surfactant, such as TRITON X-100®. The presence of BSA and surfactant minimize non-specific absorption of the analyte. A concentration of about 3% BSA and about 0.1% surfactant are effective for this purpose.

In addition, the preferred embodiment comprises distal to, or downstream of, the urine sample absorbent material a biphasic chromatographic substrate defining a release region and a capture region joined together by the fluid flow path. In the preferred configuration the release region is upstream of the capture region. The release region preferably comprises absorbent paper, and the capture medium preferably comprises nitrocellulose membrane. The release and capture media preferably are both laminated onto a transparent plastic film or sheet. Disposed upon the release medium is (1) a first binding member comprising a first monoclonal antibody reactive with a first epitope on the analyte, and labeled with a visually detectable marker, such as, colloidal gold particles and (2) a capturable component comprising a biotinylated monoclonal antibody disposed downstream of the labeled antibody. The biotinylated antibody is reactive with a second epitope on the analyte and is capable of forming a complex with the labeled antibody and the analyte. Also disposed upon the assay material is a capture site for capturing and immobilizing the complex. The capture region having immobilized thereon a capture component, preferably streptavidin, which has a high affinity for the biotin portion of the complex.

The method for manufacturing the preferred biphasic chromatographic medium is described in copending U.S. Ser. No. 08/434,342, filed on even date herewith, the disclosure of which is incorporated herein by reference. Briefly, the release region and the capture region are positioned such that they overlap slightly, and an adhesive is disposed on the back of each (the back being the side opposite that which will receive reagents). The adhesive may be any pressure sensitive or hot melt adhesive which does not fill the pores of the release or capture region, thereby permitting unimpeded flow of the solvent front through the medium. Adhesive useful in the present invention are commercially available, for example, from Adhesives Research Corp. In a currently preferred embodiment, the adhesive is disposed on a clear polymer backing. The overlapping release and capture region then are packed through laminating rollers of a laminating machine together with the backed adhesive, forming a laminate of the capture and release media, the adhesive and the polymer backing. The resulting laminated biphasic substrate then is ready to receive the reagents, which are disposed as "stripes" onto the top of the substrate. Once the reagents have been deposited and dried, if necessary, the substrate is cut into desired size.

The diffusive and non-diffusive reagents can be applied to the release and capture reagents by any well known technique. In a currently preferred embodiment, the diffusable antibody reagents are applied to the release region by direct application onto the surface of the medium and dried to form a narrow band. The non-diffusable reagents are applied to the capture region by passive adsorption.

The preferred embodiment further comprises, reservoir absorbent material disposed distal to, or downstream of, the biphasic chromatographic substrate and in fluid communication therewith. By providing a reservoir of absorbent material disposed beyond the biphasic chromatographic substrate, a relatively large volume of the urine and any analyte it contains may be drawn through the biphasic chromatographic substrate to aid sensitivity. The reservoir absorbent material preferably comprises a hydrophilic material which may be the same as the urine sample application region absorbent. The purpose of the reservoir absorbent is to facilitate capillary action along the chromatographic substrate and to absorb excess urine contained within the casing. The reservoir absorbent material preferably comprises absorbent paper made from cotton long linter fibers, such as S&S 300, S&S 470 and S&S 900 (available form Schleicher & Schuell, Inc.) or cellulosic materials, such as Whatman 3MM (available from Whatman).

During operation of the preferred embodiment, urine from a urine stream is directed through the urine sample inlet port and onto the sample application region of the assay material.

The urine then passes by sorptive transport, for example, capillary action, wicking, or simple wetting, from the urine sample application region to the biphasic chromatographic material and finally to the reservoir material. During transport through the biphasic chromatographic material the urine first contacts the first monoclonal antibody located on the release region. Upon contact with the urine, the first monoclonal antibody becomes reconstituted in the urine and then reacts with a first epitope on the pre-selected analyte, provided that the analyte is present within the urine sample. The first monoclonal antibody is labeled with a visually detectable marker such as colloidal gold. The urine while moving towards the capture region contacts the second monoclonal antibody also located in the release region. Upon contact with the urine, the second monoclonal antibody also becomes reconstituted in the urine, and then reacts with the second epitope on the pre-selected analyte. The second monoclonal antibody is labeled with a capturable component such as biotin. The analyte, first monoclonal antibody, and the second monoclonal antibody, therefore, react to form a complex which subsequently can be captured when the complex reaches the capture region and contacts the streptavidin immobilized within the capture region.

Broadly, the device and method of the invention may be used to detect any analyte which has heretofore been assayed using known immunoassay procedures, or is detectable by such procedure, using polyclonal antibodies or fragments thereof, monoclonal antibodies or fragments thereof, biosynthetic antibody binding sites or other proteins. Various specific assay protocols and reagents are known per se, see for example, U.S. Pat. No. 4,313,734, and U.S. Pat. No. 4,366,241.

It is, therefore, contemplated that the invention is not limited by the precise nature of the binding members. For example, polyclonal antibodies and fragments thereof or biosynthetic antibody sites, such as those disclosed in U.S. Pat. Nos. 5,091,513, 5,132,405, and 5,258,498 may be substituted for the monoclonal antibodies disclosed herein. Accordingly polyclonal antibodies, monoclonal antibodies or biosynthetic antibody binding sites having specific binding properties and high affinity for virtually any antigenic substance which are useful in the present invention as binding and capture materials are publicly known and available. Alternatively, preferred monoclonal antibodies, polyclonal antibodies or biosynthetic antibody binding sites may be prepared using techniques well known and thoroughly disclosed in the art. The literature is replete with protocols for producing and immobilizing antibodies. For example, the preparation of polyclonal and monoclonal antibodies is disclosed in *Antibodies, A Laboratory Manual* (1988) Harlow and Lane, Cold Spring Harbor Press. The preparation of biosynthetic antibody binding sites is described in U.S. Pat. Nos. 5,091,513, 5,132,405, and 5,258,498. Methods for immobilizing proteins are described in *Laboratory Techniques in Biochemistry and Molecular Biology*, Tijssen, vol. 15, Practice and Theory of Enzyme Immunoassays, Chapter 13, Immobilization of Immunoreactants on Solid Phases, pp. 297–328 and all the references cited therein.

In another aspect, the invention provides a method for producing an improved device for detecting the presence of an analyte in a urine stream. The method comprises providing an assay material having at least an analyte capture region for binding the analyte. The method also comprises the step of providing an outer casing. The casing defines: a hollow housing for receiving the assay material; a urine inlet port to permit urine applied directly from a urine stream to enter the casing and to contact the assay material; a window spaced apart from the urine inlet port for viewing the capture region; and at least one drainage vent to permit excess urine entering the casing through the urine inlet port to exit the casing and thereby to minimize hydraulic flooding of the casing. Finally, the method comprises the step of enclosing the assay material within the casing.

The present invention will now be further particularly described with reference to the following exemplification. In the exemplification, the test devices are described with reference to FIGS. 1 and 2 of the accompanying drawings which have been described hereinabove.

Exemplification, Pregnancy Test

In this exemplification, the performance of three types of pregnancy test devices was evaluated. The only difference between the three devices was the number and configuration of drainage vents in the casing of each device. The assay materials disposed within each casing were identical.

In a first device, as depicted in FIG. 1, the casing defined three drainage vents spaced about the urine inlet port. Briefly, one drainage vent was located at the extreme proximal end of the casing with the two remaining drainage vents located along each side of the casing. Furthermore, in this device the urine inlet port and the viewing window were disposed on opposite sides of the casing. In a second device, as depicted in FIG. 2, the casing defined a single drainage vent located on the same side of the casing as the viewing window but on an opposite side of the casing from the urine inlet port. In a third device, the casing of the device did not contain a drainage vent.

The casings for each device were formed from polystyrene by injection molding. For each device, two interlocking sections, specifically an upper section and a lower section, were prepared wherein the inner surface of the lower section of the casing defined protrusions designed to snap fit into protrusion receiving means defined by the inner surface of the upper section of the casing. Then the assay material, as defined by a urine sample absorbent material, a biphasic chromatographic substrate and a reservoir absorbent material, was enclosed within the casing to produce the device.

The same assay material array was used in each of the three devices. Briefly, the urine sample absorbent material acting as the urine sample application region was bonded hydrophilic polyester; the release medium on the biphasic chromatographic substrate was S&S 903 paper (Schleicher & Schuell); the capture medium on the biphasic chromatographic substrate was nitrocellulose membrane. The release and capture media of the biphasic chromatographic substrate were laminated onto polyethylene terephthalate precoated with an adhesive. The reservoir absorbent material was S&S 300 paper (Schleicher & Schuell) The dimensions of urine sample absorbent material were approximately 5.0×1.27×0.25 cm (2.0×0.5×0.1 inches) on each side. The dimensions of release medium of the biphasic chromatographic substrate were approximately 2.8×0.8×0.06 cm (1.1×0.32×0.025 inches), and for the capture medium, approximately 2.5×0.8×0.018 cm (1×0.32×0.007 inches). The dimensions of the reservoir absorbent pad were approximately 2.0×0.26×1.06 cm (0.8×0.1×0.4 inches). A number of these substrates were produced and further treated to adapt them for the detection of hCG in urine. The test reagents were anti-hCG monoclonal antibody 2G9 (Carter-Wallace) conjugated with 15–30 nm colloidal gold particles (Carter-Wallace); biotinylated anti-hCG specific monoclonal antibody CCF01 (Carter-Wallace); and streptavidin. The quantities of reagents used in each single-step device were 0.048 $OD_{533nm}$ 2G9 gold conjugate; 0.1 μg biotin conjugated CCF01; and 0.8 μg steptavidin. The reagents were disposed upon the assay material in the format as described hereinabove.

Protocol I. Case Study

Fifty women were each given one of the three single-step devices and asked to urinate for at least 10 seconds through the urine sample inlet port onto the urine sample application of the assay material. Each woman was to note the urination time and to record the time at which they could read a result. A monitor (a Carter-Wallace representative) also read the test result and recorded the result time. The consumers used drawings of positive, negative and invalid results to guide them; they received no help from the monitor. The consumers were asked to wait five minutes before calling a result invalid. The devices were weighed before and after testing to determine the sample volume absorbed. The performance of each device is summarized in Table I below.

It was found that all the devices used approximately the same amount of urine to perform the assay and that all of the devices had approximately the same completion time. It was found, however, that the introduction of drainage vents into the casings of devices 1 and 2 resulted in significantly higher accuracy and fewer invalid test results caused by the flooding of the assay material enclosed within the device casing. For example, 5% of the results using device 3, which had no drainage vents, were invalid because the assay material flooded. In contrast, none of the results using either devices 1 or 2, having the drainage vents, were invalid because of flooded assay material. Therefore, the introduction and placement of drainage vents in the casing dramatically improved the accuracy and reliability of the assay result.

TABLE I

| Device Type | Device 1 | Device 2 | Device 3 |
|---|---|---|---|
| Average urination time. | 15.4 seconds | 15 seconds | 16 seconds |
| Average completion time. | 1.48 minutes | 1.34 minutes | 1.52 minutes |
| % Devices run within 2 minutes. | 75% | 86% | 71% |
| % Devices run within 2 and 3 minutes. | 21% | 12% | 20% |
| % Devices run within 3 and 5 minutes. | 0% | 2% | 2% |
| % Devices run longer than 5 minutes. | 2% | 0% | 2% |
| Average Sample uptake. | 1.62 ml | 1.57 ml | 1.69 ml |
| % Invalid Results Due to Sample Flooding. | 0% | 0% | 5% |

Protocol II. High Flow Test Study

In another set of experiments designed to simulate midstream use, replicate tests were performed by adjusting the flow of water from a tap to a rate of 60–70 ml/sec and directing the water stream to the sample inlet port at the proximal end of each of the three devices. The tests were developed and the results are summarized in Table II.

The results show that, during the use of devices 1 and 2 there were no occurrences of hydraulic pressure induced flooding of the assay material disposed within the devices. On the other hand, with device 3 having no drainage vents, hydraulic pressure induced flooding of the assay material occurred in 20% of the devices. The drainage vents, therefore, dramatically improved the reliability of the assay result by minimizing the incidence of hydraulic pressure induced flooding of the assay material located within the casings of devices 1 and 2.

TABLE II

| Device Type | Device 1 | Device 2 | Device 3 |
|---|---|---|---|
| % of devices experiencing flooding of the assay material as determined by high flow tap test | 0 | 0 | 20 |

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. A single-step device for detecting the presence of an analyte in a urine stream, the device comprising:
    an assay material comprising a release medium of a first material and a releasable, visually detectable analyte binding reagent disposed thereon for release therefrom, and in fluid communication and downstream thereof, a capture medium of a second, different material and a capture reagent immobilized thereon for binding the analyte; and
    a casing defining
        a hollow housing enclosing the assay material,
        a urine inlet port through which urine applied directly from the urine stream enters the casing and contacts the assay material upstream of the release medium,
        a window spaced apart from the urine inlet port for viewing the capture medium, and
        at least one drainage vent spaced apart from the urine inlet port and upstream of the release medium through which excess urine entering the casing through the urine inlet port drains from the casing thereby minimizing hydraulic pressure induced flooding of the release medium or the capture medium of the assay material disposed within the casing.

2. A single-step device for detecting the presence of an analyte in a urine stream, the device comprising:
    an assay material comprising a urine sample application medium, in fluid communication and downstream thereof, a release medium of a first material and a releasable, visually detectable analyte binding reagent disposed thereon for release therefrom, and in fluid communication and downstream thereof, a capture medium of a second, different material and a capture reagent immobilized thereon for binding the analyte; and
    a casing defining
        a hollow housing enclosing the assay material,
        a urine inlet port adjacent the urine sample application medium through which urine applied directly from the urine stream enters the casing and contacts the assay material at the sample application medium,
        a window spaced apart from the urine inlet port for viewing the capture medium, and
        at least one drainage vent spaced apart from the urine inlet port and upstream of the release medium through which urine entering the casing through the urine inlet port drains from the casing thereby minimizing accumulation of the applied urine in an amount sufficient to flood the release medium or the capture medium of the assay material disposed within the casing.

3. The device of claim 1 or 2 wherein the casing defines three drainage vents.

4. The device of claim 1 or 2 wherein the window is located on a side of the casing opposite from the urine inlet port.

5. The device of claim 1 or 2 wherein the casing defines a single drainage vent.

6. The device of claim 1 or 2 wherein the visually detectable analyte binding reagent is a conjugate of an antibody and a visually detectable moiety.

7. The device of claim 6 wherein the antibody is a monoclonal antibody.

8. The device of claim 6 wherein the antibody is an anti-chorionic gonadotropin antibody.

9. The device of claim 6 wherein the visually detectable moiety is a colloidal gold particle.

10. The device of claim 1 or 2 wherein the release medium further comprises a biotinylated binder of the analyte releasably disposed thereon for release therefrom.

11. The device of claim 10, wherein the capture reagent is streptavidin.

12. The device of claim 1 or 2, wherein the capture medium is nitrocellulose.

13. A method for detecting the presence of an analyte in a urine stream suspected to contain the analyte, the method comprising the steps of:
    (a) providing a single-step device comprising
        an assay material comprising a release medium of a first material and a releasable, visually detectable analyte binding reagent disposed thereon for release therefrom, and in fluid communication and downstream thereof, a capture medium of a second, different material and a capture reagent immobilized thereon for binding the analyte, and
        a casing defining
            a hollow housing enclosing the assay material,
            a urine inlet port through which urine applied directly from the urine stream enters the casing and contacts the assay material upstream of the release medium,
            a window spaced apart from the urine inlet port for viewing the capture medium, and
            at least one drainage vent spaced apart from the urine inlet port and upstream of the release medium through which excess urine entering the casing through the urine inlet port drains from the casing thereby minimizing hydraulic pressure induced flooding of the release medium or the capture medium of the assay material disposed within the casing;
    (b) applying urine from the urine stream to the urine inlet port; and
    (c) observing the presence or absence of an accumulation of the visually detectable analyte binding reagent immobilized at the capture medium, the accumulation of the visually detectable analyte binding reagent being indicative of the presence of the analyte in the urine.

14. A method for producing a single-step device for detecting an analyte in urine, the method comprising:

(1) providing an assay material comprising a release medium of a first material and a releasable, visually detectable analyte binding reagent disposed thereon for release therefrom, and in fluid communication and downstream thereof, a capture medium of a second, different material and a capture reagent immobilized thereon for binding the analyte;

(2) providing a casing defining
a hollow housing for receiving the assay material,
a urine inlet port through which urine applied directly from a urine stream enters the casing and contacts the assay material at a position upstream of the release medium when disposed within the casing,
a window spaced apart from the urine inlet port for viewing the capture medium of the assay material when disposed within the casing, and
at least one drainage vent spaced apart from the urine inlet port and upstream of the release medium of the assay material when disposed within the casing through which excess urine entering the casing through the urine inlet port drains from the casing thereby minimizing hydraulic pressure induced flooding of the release medium or the capture medium of the assay material when disposed within the casing; and (3) enclosing the assay material within the casing.

15. The method of claim 14, wherein the capture medium is nitrocellulose.

16. A method for detecting the presence of an analyte in a urine stream suspected to contain the analyte, the method comprising the steps of:

(a) providing a single-step comprising
an assay material comprising a urine sample application medium, in fluid communication and downstream thereof, a release medium of a first material and a releasable, visually detectable analyte binding reagent disposed thereon for release therefrom, and in fluid communication and downstream thereof, a capture medium of a second, different material and a capture reagent immobilized thereon for binding the analyte, and
a casing defining
a hollow housing enclosing the assay material,
a urine inlet port adjacent the urine sample application medium through which urine applied directly from the urine stream enters the casing and contacts the assay material at the sample application medium,
a window spaced apart from the urine inlet port for viewing the capture medium, and
at least one drainage vent spaced apart from the urine inlet port and upstream of the release medium through which urine entering the casing through the urine inlet port drains from the casing thereby minimizing accumulation of the applied urine in an amount sufficient to flood the release medium or the capture medium of the assay material disposed within the casing;

(b) applying urine from the urine stream to the urine inlet port; and (c) observing the presence or absence of an accumulation of the visually detectable analyte binding reagent immobilized at the capture medium, the accumulation of the visually detectable analyte binding reagent being indicative of the presence of the analyte in the urine.

* * * * *